US008217187B2

(12) United States Patent
Yee et al.

(10) Patent No.: US 8,217,187 B2
(45) Date of Patent: *Jul. 10, 2012

(54) PROCESS TO EXTRACT QUASSINOIDS

(75) Inventors: Trevor Herbert Yee, Kingston (JM); Helen Marjorie Jacobs, Kingston (JM)

(73) Assignee: The University of the West Indies, Kingston (JM)

( * ) Notice: Subject to any disclaimer, the term of this patent is extended or adjusted under 35 U.S.C. 154(b) by 829 days.

This patent is subject to a terminal disclaimer.

(21) Appl. No.: 12/181,412

(22) Filed: Jul. 29, 2008

(65) Prior Publication Data

US 2009/0171102 A1 Jul. 2, 2009

Related U.S. Application Data

(63) Continuation of application No. 11/450,423, filed on Jun. 12, 2006, now Pat. No. 7,404,972.

(60) Provisional application No. 60/734,771, filed on Nov. 9, 2005.

(51) Int. Cl.
C07D 407/00 (2006.01)

(52) U.S. Cl. ...................................... 549/278

(58) Field of Classification Search .................. 549/278
See application file for complete search history.

(56) References Cited

U.S. PATENT DOCUMENTS 7,404,972 B2   7/2008 Yee et al.

FOREIGN PATENT DOCUMENTS

WO   WO-2005092329 A1   10/2005

OTHER PUBLICATIONS

Adams et al., "The Amaroids of Quassia. I. Quassin, Isoquassin and Neoquassin," Journal of The American Chemical Society, vol. 72, Jan. 1950, pp. 375-379.

Clark, "Quassin. I. The Preparation and Purification of Quassin and Neoquassin, with Information Concerning their Molecular Formulas," Journal of The American Chemical Society, vol. 59, May 1937, pp. 927-931.

Clark, "Quassin. IV. A Minor Constituent of Jamaica Quassia Wood," Journal of the American Chemical Society, vol. 64, Dec. 1942, pp. 2883-2884.

Guo Z, Vangapandu S, Sindelar RW, Walker LA, Sindelar RD, "Biologically active quassinoids and their chemistry: potential leads for drugdesign," Current Medicinal Chemistry, Jan. 2005;vol. 12(2):173-190.

Okano et al., "Biologically Active Compounds from Simaroubaceous Plants," Studies in Natural Products Chemistry, vol. 7, 1990, pp. 369-404, Elsevier Science Publishing Company Inc., New York, New York.

Polonsky, "Chemistry and Biological Acitvity of the Quassinoids," Chemistry and Chemical Taxonomy of the Rutales, 1983, p. 247-266.

*Primary Examiner* — Andrew D Kosar
*Assistant Examiner* — Raymond Covington
(74) *Attorney, Agent, or Firm* — Wilmer Cutler Pickering Hale and Dorr LLP

(57) ABSTRACT

A means for the extraction and crystallization of quassinoids such as quassin and neoquassin from natural sources containing these compounds, using compounds that are Generally Recognized As Safe by the U.S. Food and Drug Administration is provided. In particular, a means for extraction that does not require use of lead acetate, chloroform, methanol, or diethyl ether is provided. The process includes a means of removing non-polar and very polar substances from an extracted residue to enhance crystallization of quassinoids from the residue.

31 Claims, 6 Drawing Sheets

R=H

| COUNTRIES OF EXPORT | YEAR: 1999 | | YEAR: 2000 | | YEAR: 2001 | |
|---|---|---|---|---|---|---|
| | Kg | F O B Ja$ | Kg | F O B Ja$ | Kg | F O B Ja$ |
| U.K. | 32,250 | 1,890,203 | 51,240 | 3,277,295 | 39,000 | 2,668,205 |
| U.S.A. | 90 | 5,117 | - | - | 1,000 | 66,367 |
| France | 12,000 | 666,618 | 17,250 | 1,092,384 | 43,291 | 1,544,217 |
| Germany | 6,250 | 360,795 | 3,000 | 183,774 | - | - |
| Italy | 21,750 | 1,269,341 | 27,525 | 1,900,046 | 35,500 | 2,584,062 |
| Spain | 6,000 | 57,0067 | - | - | - | - |
| TOTAL | 78,340 | 4,762,141 | 99,015 | 6,453499 | 118,791 | 6,862,851 |

1 = Crystaline mixture of quassin/neoquassin
2 = Extract from wood chips

PROCESS TO EXTRACT QUASSINOIDS

RELATED APPLICATION

This application is a continuation of application Ser. No. 11/450,423 filed Jun. 12, 2006 now U.S. Pat. No. 7,404,972, which claims the benefit of U.S. Provisional Application No. 60/734,771 filed Nov. 9, 2005 (incorporated herein by reference), and which is related to Jamaican Application 18/1/4370 filed Jun. 13, 2005 (incorporated herein by reference).

FIELD OF THE INVENTION

This invention relates generally to an extraction process. More specifically, it is a process for the extraction of quassinoids such as quassin and/or neoquassin from natural substances such as plants in the family Simaroubaceae.

BACKGROUND OF THE INVENTION

The Jamaican Quassia or Bitterwood, *Picrasma excelsa* is a member of the plant family Simaroubaceae in the order Sapindales. It is a tree, 6-25 meters tall, native to the Greater Antilles of the West Indies, and is common in various localities in Jamaica. See, Adams, C. D. *Flowering Plants of Jamaica*. 1972. University Press, Glasgow, p. 390. Other members of this family include for example, *Quassia amara, Picrasma quassioides*, and *Quassia africana*

Quassin and neoquassin (FIGS. 1 and 2), are used in alcoholic beverages, e.g. aperitifs such as Campari™, and other beverages and grapefruit flavoured drinks, such as Ting™. See for example, Coyle, L. P. *The World Encyclopedia of Foods*. Facts On File, Inc., New York, 1982, p. 543.

Quassin and neoquassin have been reported to stimulate the appetite and to aid digestion; and because of these properties they are ingredients of aperitifs, and are also used in the treatment of the eating disorder, anorexia nervosa. See for example, Bown, D. *The Royal Horticultural Society Encyclopedia of Herbs and Their Uses*, 1995, Dorling Kindersley, London, p. 327; and Chavalier, A. The Dorling Kindersley Encyclopedia of Herbal Medicine. 2000. Dorling Kindersley, p. 247.

Quassinoids have also been indicated in the use of medicaments due to biological activity such as anti-malarial, anti-insecticidal, anti-amoebicidal, anti-leukemic, and anti-viral properties. See for example, U.S. Pat. No. 5,639,712 to Grieco et al.

Jamaica has been an important source of quassin and neoquassin, and traditionally, dried wood chips of *P. excelsa* have been exported; and from these a mixture of quassin and neoquassin has been extracted overseas. Data from the Statistical Institute of Jamaica (STATIN) show that approximately 119 tons of wood chips were exported in 2001 at a value of approx. J$7M. See for example, FIG. 3 from The Statistical Institute of Jamaica, STATIN.

There is a need for a process that will produce quassinoids such as quassin and/or neoquassin in crystalline form, as this would afford the marketing of a purified end product. The development of such a process would also lead to the possibility of local processing with the economic benefits of exporting a value added product, providing local employment, etc.

The quassin/neoquassin content of the wood of *Picrasma excelsa*, Jamaican Quassia, and of *Quassia amara*, Surinam Quassia, has recently been quantified analytically by UV spectrophometry and by analytical HPLC. See for example, Villalobos, R; Marmillod, D; Ocampo, R; Mora, G; Rojas, C. Acta Hort (ISHS), 1999, 502, 369-376. Variations in the quassin and neoquassin content in *Quassia amara* (Simaroubaceae) in Costa Rica: Ecological and management implications. Also see Nestler, T; Tittel, G; Wagner, H. *Planta Med.* 1980.38, 204-213. Quantitative estimation of bitter quassinoids in *Quassia amara* and *Picrasma excelsa*; and Sugimoto, N; Sato, K; Yamakaki, T; Tanamoto, K. Shokuhin Eiseigaku Sasshi. 2003. 44, 328-331. Analysis of constituents in Jamaican quassia extract, a natural bittering agent.

The percentages of total bitter substances are reported to range from 0.14 to 0.28%. In *P. excelsa*, quassin and neoquassin were detected in equal quantities, 0.09% each, and these were found to comprise the total bitter substances in this wood (0.18%). The isolation of quassin/neoquassin from wood of *Q. amara* and *P. excelsa* described by Clark results in yields of 0.15 to 0.18%, and 0.1% respectively. See for example, Clarke, E. P. *J. Am. Chem. Soc.* 1937. 59, 927-931. The preparation and purification of quassin and neoquassin, with information concerning their molecular formulas; and Clarke, E. P. *J. Am. Chem. Soc.* 1938. 60, 1146-1148. Quassin III. Picrasmin. The same process is used for the wood of both species. This entails extraction of the wood with hot water, treatment of the aqueous extract with lead acetate and carbon, trituration of the resulting solid with chloroform, evaporation of the chloroform and finally crystallization of the quassinoid mixture from aqueous methanol. The British Pharmaceutical Codex (BPC) method of 1911 requires extraction of *P. excelsa* wood with 50% alcohol, neutralization of the extract with MgO, acidification with tartaric acid followed by evaporation of the alcohol and extraction of the residue with chloroform; the crystalline quassinoids are obtained from the chloroform extract by removal of the solvent and crystallization from alcohol-diethyl ether mixtures. No yields are reported for this BPC method. See for example, *British Pharmaceutical Codex*. The Pharmaceutical Press: London, 1911. Quassinum.

The BPC of 1949 describes only a method for preparation of an aqueous crude extract of quassia based on cold percolation with water; subsequent codices do not provide isolation methods for quassin-neoquassin. See for example, *British Pharmaceutical Codex*. The Pharmaceutical Press: London, 1949: p 1129, Extractum Quassiae; and *British Pharmaceutical Codex*. The Pharmaceutical Press: London, 1973, p 422. Quassia.

All preparative scale isolation methods leading to clean mixtures of quassin/neoquassin described thus far, entail the use of one or more of the toxic, or carcinogenic or otherwise hazardous, or banned substances: lead acetate, chloroform, methanol, diethyl ether. There therefore continues to be a need for an isolation method that does not require the use of such substances.

SUMMARY OF THE INVENTION

The invention comprises a process for the extraction of quassinoids such as quassin and/or neoquassin from natural sources containing these compounds. An extract derived from natural sources is dispersed in a first solvent. The nonpolar contaminants are removed through the addition of a second solvent that is immiscible in the first solvent and that has a lower polarity than the first solvent. A polarity increasing means is then added such as a quantity of a non-toxic neutral salt. Through these steps a residue results that no longer has polar and nonpolar contaminants and can be subjected to crystallization to yield crystalline quassinoid(s).

It is an object of the present invention to provide a process for the extraction of a quassinoids from plants of the plant family Simaroubaceae such as *Picrasma excelsa*, (Jamaican Quassia); *Quassia amara*, (Surinam Quassia), *Picrasma quassioides*, or *Quassia africana*.

It is a further object of the present invention to provide a process that will produce the active ingredients in crystalline form.

It is a further object of the present invention to provide preparative scale isolation method(s) leading to quassin, neoquassin, or a mixture thereof that do not entail the use of lead acetate, chloroform, methanol, or diethyl ether.

It is a further object of the present invention to provide a process that comprises the use of compounds that are Generally Recognized As Safe (GRAS) by the Food and Drug Administration.

It is a further object of the present invention to improve cold percolation extraction with a process that reduces the required time and energy.

It is a further object of the present invention to provide a process to obtain crystalline quassin, neoquassin, or a mixture thereof with 24 hour extraction.

It is a further object of the present invention to provide processes directed both to highly purified crystalline mixtures and to crystalline mixtures of lesser purity.

There have thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced or carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

The references that are cited within this application are herein each incorporated by reference in its respective entirety.

For a better understanding of the invention, its operating advantages and the specific objects attained by its uses, reference should be had to the accompanying drawings and descriptive matter, which illustrate preferred embodiments of the invention.

BRIEF DESCRIPTION OF THE DRAWINGS AND FIGURES

DETAILED DESCRIPTION OF THE INVENTION

Figure 1:
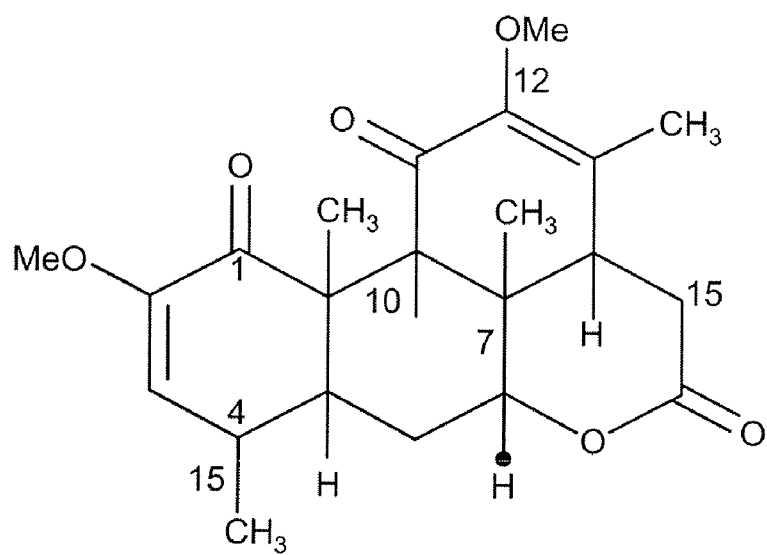
FIG. 1 illustrates the structure of quassin.
Figure 2:
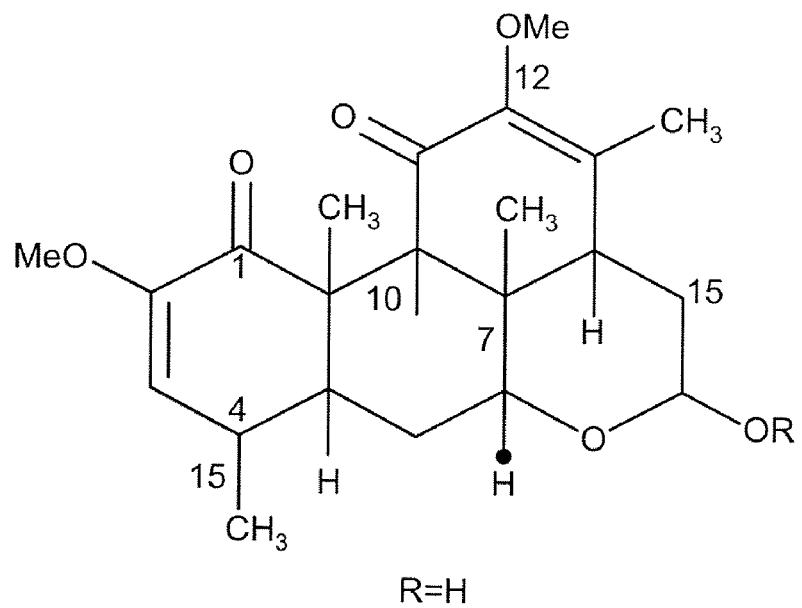
FIG. 2 illustrates the structure of neoquassin.

A system and method are disclosed herein for the extraction and crystallization of quassinoids such as quassin and/or neoquassin. While the illustrative examples are directed to Bitterwood, alternative natural sources of quassinoids are contemplated. The embodiments disclosed herein are disclosed for illustrative purposes only, alternative embodiments are envisioned. The initial embodiment of the present invention is two step: a solvent extraction sequence leading to a crystalline mixture of the active ingredients; and the extraction of additional crystalline active ingredients from the mother liquor of the first crystallization by a chromatographic method. As used herein, mother liquor is understood to mean the impure or complex residual solution that remains after the substances/materials readily or regularly crystallizing have been removed. Further embodiments describe a more efficient extraction method using ultrasonic agitation and a simplified crystallization process to obtain an impure crystalline mixture.

OVERVIEW

The amount of quassin/neoquassin in wood chips of *P. excelsa* and *Q. amara* has been reported as being between 0.1-0.2% w/w. In the first step using the initial embodiment disclosed herein, a yield of 0.06% w/w of a crystalline mixture of the active ingredients was obtained. As a comparison, the yields of the crystalline mixture from column chromatography on residues extracted from Bitterwood chips from hot and cold percolation with ethanol were determined as 0.021% and 0.102% w/w respectively. Percolation with other solvents and subsequent column chromatography showed that the percolation in cold ethanol gave the best yield of the crystalline mixture of quassin/neoquassin. In the second step of the initial embodiment, an additional 0.066% w/w of crystalline active ingredients was obtained. In an alternative embodiment of the present invention, wherein a simplified crystallization process is used to obtain an impure crystalline mixture, the yield of impure crystalline material obtained from the wood chips was approx. 0.3% w/w.

The preferred embodiment of the present invention comprises the use of non-polar solvents and alcohols that are Generally Recognized As Safe (GRAS) by the Food and Drug Administration. Alternative substances include for example, substituting petroleum ether for hexane or methanol for ethanol. Additional GRAS and non-GRAS alternatives are in the scope of one of ordinary skill in the art.

Initial Embodiment

Step 1. Initial Process to Obtain the Active Ingredients from Bitterwood, Quassin/Neoquassin in a Crystalline Mixture Because of the relatively low concentration of quassin/neoquassin in the wood chips, attempted direct crystallizations of the gum or residue extracted from the wood chips, with a number of solvent systems were routinely unsuccessful.

A number of solvents were evaluated, including water, dichloromethane and ethyl acetate for the amount of quassin/neoquassin extracted by each solvent and the purity of the resulting extracts. After a series of trials it was found that percolation of wood chips with cold ethanol gave the highest yield of quassin/neoquassin, as determined by separation with column chromatography. It was unexpected that the yield of quassin/neoquassin would be higher when the wood chips were percolated with cold as compared to hot, refluxing ethanol. Cold ethanol percolation was seen to be the preferred solvent extraction means.

Figures 3, 4:
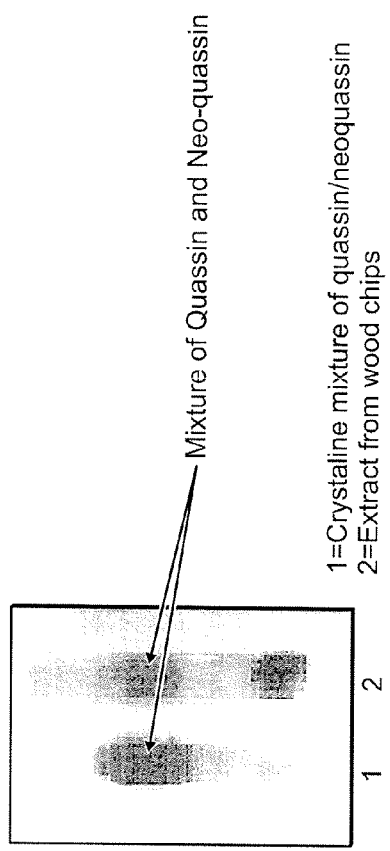
FIG. 3 illustrates quassin chips export for the years 1999-2001.
FIG. 4 illustrates thin layer chromatogram of the residue resulting from cold ethanol percolation and evaporation of solvent.

Thin layer chromatography of the residue resulting from the cold ethanol percolation and evaporation of the solvent, showed a fairly complex mixture but suggested a possible methodology for the extraction of the active ingredients (FIG. 4). However, while chromatography could provide a method to obtain relatively pure quassin/neoquassin from the extracted gum or residue, it was likely to be too expensive as the basis for an industrial process. Thus, experimentation continued to devise a more commercially suitable process.

From the thin layer chromatogram of the extracted gum or residue obtained from solvent extraction of Bitterwood, it was observed that the active ingredients of quassin/neoquassin appeared in the middle region of the chromatogram. In attempting to crystallize the extracted residue, crystallization was prevented either by the presence of very polar substances, which tended to precipitate out during attempts at crystallization, or by non-polar substances, which resulted in an oily fraction, from which crystallization was difficult or impossible. It was therefore postulated that if a process could be devised that would remove both the non-polar and very polar substances, then the residue that remained would likely be sufficiently purified to be crystallizable. This hypothesis proved to be correct.

Extraction of Bitterwood chips by refluxing in water, and subsequent evaporation of the water yielded a hard residue that was relatively free of non-polar compounds. The residue had a high concentration of the very polar substances, and was difficult to dissolve in the common organic solvents, e.g. ethyl acetate, dichloromethane, etc.

By dissolving the water extracted residue in water with a little heat to aid the dissolution, saturating the aqueous extract with a salt such as sodium chloride, and extracting with ethyl acetate, it was found that almost all of the quassin/neoquassin contained in the residue dissolved in the ethyl acetate fraction, leaving behind the very polar components in the aqueous fraction.

Because of the high bitterness index of quassin/neoquassin, reported at 1 part in 60,000 and even as high as 1 part in 250,000, a simple method to test the completeness of extraction is to taste the fractions. See for example, The Merck Index, Ninth Edition. 1976. Merck & Co. Inc., Rahway, N.J., USA, p. 1042; and The Code of Federal Regulations, U.S. National Archives and Records Administration. 2004. p. 499. By this very sensitive taste test, it was determined that the residual active ingredients in the aqueous fraction was negligible and that they were almost quantitatively contained in the ethyl acetate fraction.

Attempted crystallization of an ethanol solution of the residue resulting from evaporation of the ethyl acetate was successful and crystallization induced either by scratching the sides of the container or more easily by seeding with crystals of quassin/neoquassin. The thin layer chromatogram of the crystals obtained indicated that the mixture was quassin/neoquassin.

Step 2. Process to Obtain Additional Crystals of Quassin/Neoquassin from the Residue Resulting from Step 1

Further crystallization from the mother liquor remaining after crystallization of the residue from step 1, was desired. While a variety of chromatographic methods were contemplated, a simple and cost effective method was preferred. Thus, the goal was the removal of the non-polar and very polar substances by a chromatographic process, with the intended result of a fraction enriched in the crystalline active ingredients, and therefore crystallizable.

Preferably a relatively inexpensive grade of silica was to be used. In a preferred embodiment this grade of silica is 60-120 mesh. Also it was preferred to have a relatively low ratio of silica to residue being separated.

There were three considerations with regard to the choice of solvents: 1/ the number of solvents should preferably be kept at a minimum; 2/ preferably the solvents should be pure or relatively pure, so that they could be recovered by evaporation for reuse in the process; and 3/ preferably the first solvent should be effective in removing the non-polar substances but not the active ingredients.

In a first embodiment aimed at separation, a simple system of hexane initially followed by ethyl acetate was used, with a silica to residue ratio of 20:1. In this embodiment, the hexane removed only non-polar substances but did not do so completely. The result was that the second fraction, obtained by eluting with ethyl acetate, crystallized with considerable difficulty and the thin layer chromatogram indicated the presence of enough non-polar substances to make the process difficult.

A crystallizable fraction could be obtained by using 20% ethyl acetate in hexane as the first solvent followed by ethyl acetate. The thin layer chromatogram of the ethyl acetate fraction showed that it contained primarily quassin/neoquassin, and it crystallized upon seeding. This process, though effective, involved the use of solvent mixtures and did not achieve our goal of using pure or single solvents. It was reasoned that by reducing the ratio of silica to residue, the solvent power of the hexane fraction would be increased and one might be able to remove sufficient non-polar substances to induce crystallization.

However, too low a ratio of silica to residue being separated would in effect increase the solvent power of the second eluting solvent, ethyl acetate, promoting the extraction of the very polar substances in addition to the active ingredients. During experimentation with several ratios of silica to mother liquor residue, it was found that with a ratio of 20:1 silica to residue, the hexane fraction did not remove the non-polar substance to an optimum level, and the ethyl acetate fraction would not crystallize. At a ratio of 15:1 silica to residue, the hexane fraction removed the non-polar substances, but also removed some of the quassin/neoquassin mixture.

The desired separation was achieved by using a silica to residue ratio of 17:1. In the event three fractions were eluted, fraction one with hexane, contained only non-polar substances, fraction two with ethyl acetate, had a high concentration of the desired quassin/neoquassin mixture and fraction three, which was an elution with ethanol to strip the column, showed only a trace of quassin/neoquassin, by thin layer chromatography.

Seeding of fraction two afforded a crystalline mixture of the desired quassin/neoquassin.

Second Embodiment

Although the above extraction method achieved the goal of removing both the non-polar substances and the very polar ones, and resulted in a reproducible method for obtaining mixed crystals of quassin/neoquassin, there were two drawbacks with it as a basis for a commercial process. First, the refluxing of the wood chips with water and the removal of the water after the process are highly energy consuming. An easier and more cost effective of achieving the desired extraction was desired. Second, after a comparison of extraction with various solvents, cold percolation with ethanol proved to be the most effective method in terms of yield of the active ingredients. This latter process was also the more energy efficient, as it involved the evaporation of ethanol as compared to water. However, the residue obtained as previously described (cold ethanol extract, dissolution in water, saturation of the aqueous solution with sodium chloride followed by extraction with ethyl acetate) resisted all attempts at crystallization by seeding. It was concluded that this was likely because there was too large a non-polar fraction in the mixture. This explanation was supported by the thin layer chromatogram.

The following adaptation to the methodology achieved the goal of removal of both the non-polar and very polar substances and resulted in a residue from which a crystalline mixture of quassin/neoquassin was obtained.

To remove the excess non-polar substances, the mixture obtained from the extraction by cold percolation of Bitterwood chips with ethanol, evaporation of ethanol, and dissolution/suspension in water, was washed with a non-polar solvent such as hexane, before the saturation of the mixture with sodium chloride and extraction with ethyl acetate. In order not to remove any of the active ingredients of quassin/neoquassin, at this stage, it was thought best to extract before increasing the polarity of the aqueous fraction.

The thin layer chromatogram of the hexane extract confirmed that only non-polar substances were being removed by this adaptation and this was supported by the taste test.

Having removed the non-polar substances, the aqueous mixture was then saturated with sodium chloride and then extracted with ethyl acetate. Sodium chloride is a preferred means of increasing the polarity of the aqueous fraction due to its low cost and GRAS status. However, alternative salt substitutes are contemplated. The taste test of the extracts confirmed that the quassin/neoquassin mixture was almost quantitatively extracted by the ethyl acetate. Evaporation of the ethyl acetate produced a residue, which when seeded successfully yielded a crystalline mixture of quassin/neoquassin.

Figure 5:
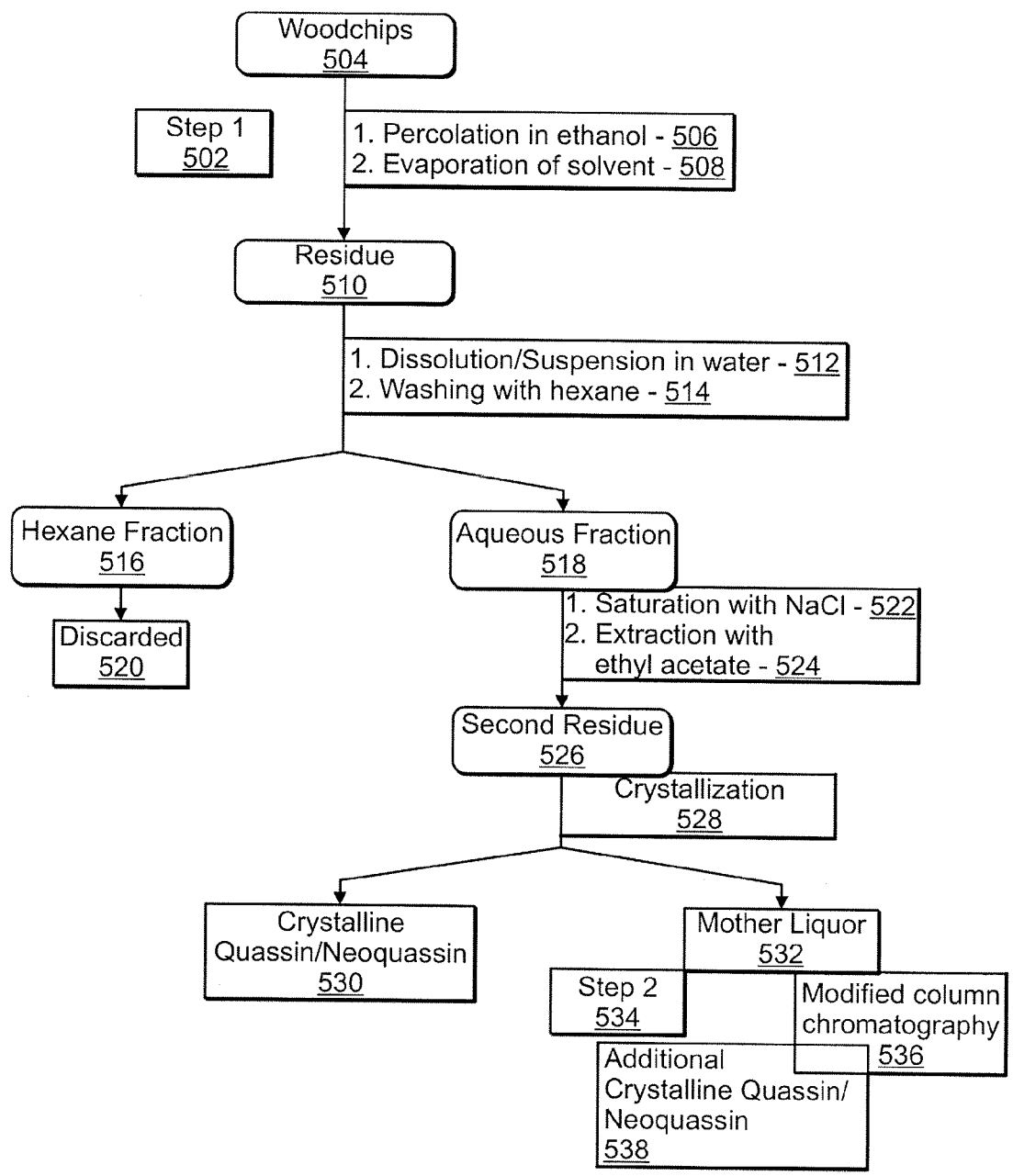
FIG. 5 illustrates a schematic diagram of the extraction process for the active ingredients of Bitterwood.

FIG. 5 illustrates this revised process. As shown, in Step One 502, woodchips 504 are percolated in a solvent 506. In a preferred embodiment, the solvent is ethanol. Evaporation of solvent 508 yields residue 510. Residue 510 is then dissolved/suspended in water 512 and washed with hexane 514 resulting in hexane fraction 516 and aqueous fraction 518. Hexane fraction 516 is discarded 520. Aqueous fraction 518 is saturated with sodium chloride 522 and extracted with ethyl acetate 524, resulting in second residue 526.

Second residue 526 is then subjected to crystallization 528. Crystallization 528 yields crystalline quassin/neoquassin 530 and mother liquor 532. In step two 534 mother liquor 532 is subjected to modified column chromatography 536 resulting in additional crystalline quassin/neoquassin 538.

Additional Embodiment

In an effort to further improve the process for a commercial extraction of quassin and neoquassin from Bitterwood chips or from other natural sources, further optimizations to the process were explored, in both the extraction stage and in the crystallization stage.

The Extraction Stage

The extraction of the quassin/neoquassin, initially as a residue from Bitterwood chips, by cold mixing or percolation with ethanol was previously described herein. As mentioned, attempts to increase the rate of extraction by heating resulted in a lower yield than that obtained with a cold percolation. In practice, however, the extraction by the cold percolation method requires several days to a week or more to extract most of the active ingredients. A process that would reduce the time required for the percolation process, and avoid the energy and time consuming activities associated with cold percolation: repeated concentration, recovery and re-use of solvent, was desired. In this extraction improvement effort, a method was determined by which the quassin and neoquassin contained in the wood chips are quantitatively extracted in a period of 24 hours. After this period the wood chips lose all their bitterness when tasted, and further extraction yields no additional residue containing quassin/neoquassin.

The experimental method employed used an ultrasonic bath as an agitator and a 1:1 v/v mixture of ethanol and water, at room temperature, as the extracting solvent. See for example, Celeghini, R. M. S; Vilegas, J. H. Y; Lancas, F. M. *J. Braz. Chem. Soc.* 2001, 12, 706-709. After sonification of the wood chips for 24 hours, the ethanol was removed by a rotary evaporator, and the remaining mixture was extracted firstly with hexane, then saturated with sodium chloride, and extracted with ethyl acetate in the manner previously described for the cold percolation extraction, to afford a residue that contained quassin/neoquassin.

The residue obtained from this extraction was similar to that obtained from the cold percolation of the chips with ethanol, and eventually yielded a crystalline mixture of quassin/neoquassin, by the previously described sequence of solvent partitioning followed by crystallization by seeding from a solution in ethanol. The advantage was that by using sonification, the extraction process was reduced to 24 hours, and was complete after this time.

The Crystallization Stage

Processes disclosed thus far were directed to a highly purified crystalline mixture of quassin/neoquassin. However, impure crystals that are of a pale yellow to slightly amber color are also an important commerce product. Accordingly, the process was also optimized to produce a crystalline mixture similar to the accepted item of commerce. This is obtained by stirring a solution of the ethyl acetate extract, derived as described above, in either ethyl acetate or ethanol, with 2.5 to 5.0% w/w activated charcoal. See for example, Furniss, B; Hannaford, A. J; Smith, P. W. G; Tatchell, A. R., Revisors. 1989. *Vogel's Textbook of Practical Organic Chemistry*. Addison Wesley Longman Limited. Essex, England. p. 140. By this method, the charcoal removes enough of the dark colored impurities of the residue to leave a pale yellow/amber solution. Thin layer chromatography indicated that this pale yellow/amber solution was primarily a mixture of quassin and neoquassin. Evaporation of the solvent after decolorization with the activated charcoal, and dissolution of the resulting residue in ethanol afforded a crystallizable solution. When this ethanol solution was seeded with a pure sample of crystalline quassin/neoquassin and the solvent allowed to slowly evaporate at room temperature to the point of drying out, a pale yellow crystalline solid resulted; and this solid could be removed by scraping from the crystallizing flask. Thin layer chromatography indicated that the major component of this solid was quassin/neoquassin.

Figure 6:
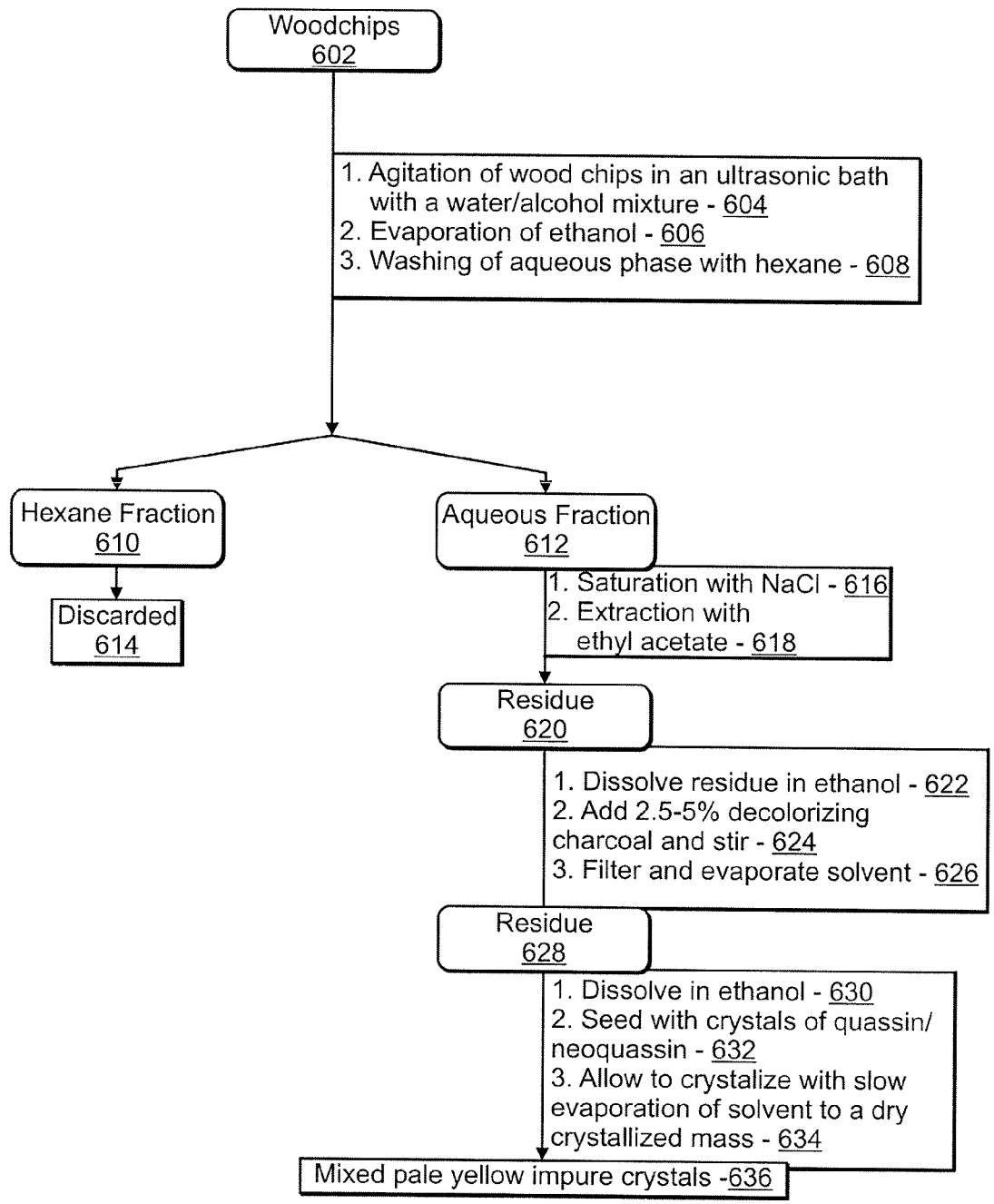
FIG. 6 illustrates a revised schematic diagram of the extraction process for the active ingredients of Bitterwood, with variation to the extraction and crystallization steps to produce an impure crystalline mixture of quassin/neoquassin.

An illustration of this alternate process is given in FIG. 6. As shown, woodchips 602 are agitated in an ultrasonic bath with a water/alcohol mixture 604, the alcohol is evaporated 606, and the aqueous phase is washed with hexane 606 to yield hexane fraction 610 and aqueous fraction 612. Hexane fraction 610 is discarded 614. Aqueous fraction 612 is saturated with NaCl 616 and extracted with ethyl acetate 618 to yield residue 620. Residue 620 is then dissolved in a solvent. Preferably this solvent is an alcohol and preferably the alcohol is ethanol 622. Decolorizing charcoal is added and the resulting suspension is stirred 624. Preferably 2.5% to 5% decolorizing charcoal is used. The resulting suspension is filtered and the solvent evaporated 626, resulting in second residue 628. Second residue 628 is then dissolved in a solvent 630, seeded with crystals of quassin/neoquassin 632 and allowed to crystallize with slow evaporation of solvent to form a dry crystallized mass 634. Preferably the solvent is an alcohol and preferably the alcohol is ethanol. Preferably said crystallized mass is mixed pale yellow impure crystals 636.

Figure 7A:
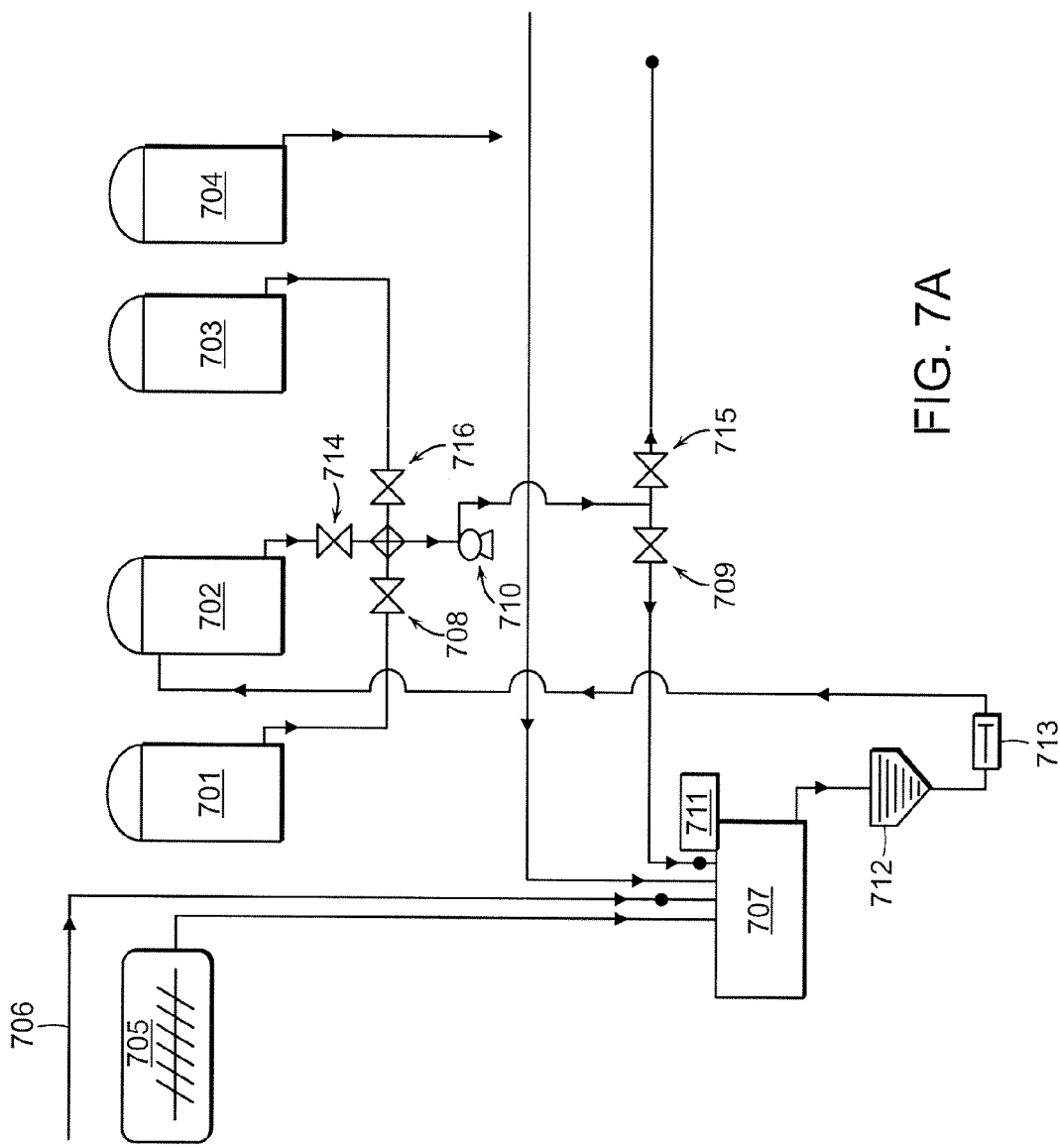
FIGS. 7A and 7B illustrate an extraction process and method.
Figure 7B:
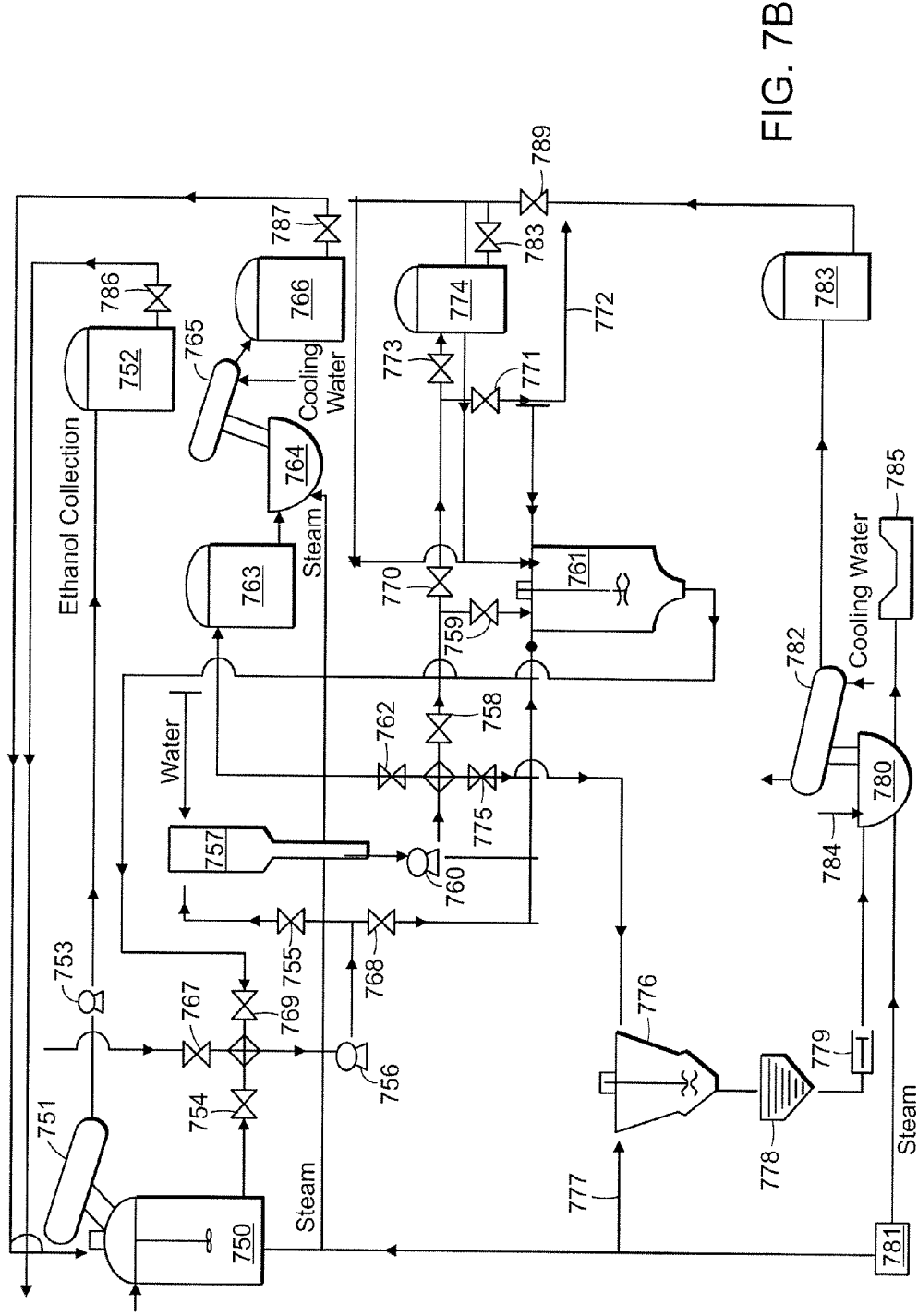

FIGS. 7A and 7B illustrate an extraction process and method. As shown, a plurality of containers store fluids, ethanol tank 701, ethanol water solution tank 702, hexane tank 703 and ethyl acetate tank 704 are disclosed in the illustration of FIG. 7A. A plurality of valves control fluid flow, each valve having an open and a closed position. The valves are controlled by a plurality of pumps.

As the process begins all valves are closed. Chips from chipper 705 and water from city water 706 flow through conduits to ultrasonic bath 707. First valve 708 and second valve 709 are opened with first pump 710 to allow for ethanol flow from ethanol tank 701 to ultrasonic bath 707. Once the desired amount of ethanol has been dispensed, as determined by meter 711, first valve 708 and second valve 709 are closed. Ultrasonic bath 707 is then activated for the desired amount of time resulting in an ethanol/water extraction solution. The ethanol/water extraction solution is directed to filter 712 and directed via second pump 713 to ethanol/water tank 702. The components of step one are repeated until a designated amount of ethanol/water extraction solution has been obtained and is stored in ethanol/water solution tank 702

Upon completion of step one, third valve 714 and fourth valve 715 are opened with first pump 710 to provide for flow of ethanol/water extraction solution from ethanol/water solution tank 702 to jacketed or coiled still 750, as shown on FIGS. 7A and 7B. Once complete, third valve 714 and fourth valve 715 are closed, the boiler is initiated, ethanol vapor is condensed by first condenser 751 and directed to ethanol collection tank 752 by vacuum pump 753 and ethanol is distilled off. The remaining water phase is cooled in still, using city water. Fourth valve 715 and fifth valve 716 are opened with first pump 710 to allow for hexane flow from hexane tank 703 to jacketed or coiled still 750. Once the desired amount of hexane has been dispensed, fourth valve 715 and fifth valve 716 are closed and the resulting solution within jacketed or coiled still 750 is agitated thoroughly, thereby completing step two and forming hexane/water mixture.

Sixth valve 754 and seventh valve 755 are opened with third pump 756 to allow for hexane water mixture flow from jacketed or coiled still 750 to separator 757 to create a separated water phase. Once transfer is completed, sixth valve 754 and seventh valve 755 are closed. Eighth valve 758 and ninth valve 759 are then opened with fourth pump 760 to allow for transfer of separated water phase from separator 757 to salting tank 761. Once transfer is complete, eighth valve 758 and ninth valve 759 are closed. Salt is added to salting tank 761 and the resulting solution/suspension is agitated. Tenth valve 762 is opened to allow for transfer of hexane via fourth pump 760 from separator 757 to hexane recovery tank 763 for recovery using evaporator 764. Tenth valve 762 is closed, vapor from evaporator 764 is condensed in second condenser 765 and collected in purified hexane collector 766, thereby completing step three.

Step four begins by saturating the water phase in salting tank 761, with sodium chloride. Eleventh valve 767 and twelfth valve 768 are opened with third pump 756, and the required amount of ethyl acetate is transferred into salting tank 761. Eleventh valve 767 and twelfth valve 768 are closed and the saturated water/ethyl acetate mixture is agitated thoroughly. Thirteenth valve 769 and seventh valve 755 are opened, saturated water/ethyl acetate mixture is transferred from salting tank 761 to separator 757 via third pump 756. Thirteenth valve 769 and seventh valve 755 are closed. Eighth valve 758, fourteenth valve 770 and fifteenth valve 771 are opened and water phase from separator 757 is pumped to waste water line 772 via fourth pump 760. Eighth valve 758, fourteenth valve 770 and fifteenth valve 771 are closed. City water is used to wash salting tank 761 and discard wash water to waste. The sodium chloride washing cycle is then begun. This cycle is initiated by opening eighth valve 758 and ninth valve 759 and with fourth pump 760 allowing for transfer from separator 757 to salting tank 761. Eighth valve 758 and ninth valve 759 are then closed. The required amount of city water is added to the salting tank, and the resulting solution/suspension is thoroughly agitated in order to wash excess NaCl from the ethyl acetate. Seventh valve 755 and thirteenth valve 769 are again opened, and with third pump 756, transfer mixture from salting tank 761 to separator 757. Seventh valve 755 and thirteenth valve 769 are then closed. Eighth valve 758, fourteenth valve 770 and sixteenth valve 773 are opened, and with fourth pump 760 pump water phase to water collection tank 774. Eighth valve 758, fourteenth valve 770 and sixteenth valve 773 are closed. The sodium chloride washing cycle is repeated until the washing of sodium chloride from the ethyl acetate is satisfactorily completed. Then, seventeenth valve 775 is opened and with fourth pump 760, the washed ethyl acetate is transferred to clarifier 776. Seventeenth valve 775 is then closed.

In step five the required amount of charcoal 777 is added and the resulting combination is agitated. The combination is filtered by filter 778 to yield filtered ethyl acetate. Fifth pump 779 transfers filtered ethyl acetate from clarifier 776 via filter 778 to evaporator 780.

In step six, boiler 781 is initiated. Evaporated ethyl acetate is condensed in condenser 782 and routed to ethyl acetate collection tank 783. Ethanol 784 is added to evaporator 780 to form a thick liquor. This mixture is transferred to crystallizer 785 and seeded to induce crystallization.

During this process solvents are reused. For example: 1/ eighteenth valve 786 is opened and distilled ethanol is directed from ethanol collection tank 752 to ultrasonic bath 707; 2/ nineteenth valve 787 is opened and distilled hexane is directed from hexane collection tank 766 to jacketed still 750; 3/ twentieth valve 788 is opened and wash water is directed from wash water collection tank 774 to salting tank 761; and 4/ twenty-first valve 789 is opened and evaporated ethyl acetate is directed from ethyl acetate collection tank 783 to salting tank 761.

By this simplified crystallization procedure the yield of crystalline end product improved to approx. 0.3%, based on the weight of the wood chips extracted and the product was a pale yellow/amber crystalline mixture, deemed acceptable to the trade, and which consisted predominantly of quassin/neoquassin. The quassin/neoquassin content of this crystalline mixture was 39%; and this was established by isolation with using column chromatography. See for example, Still, W. C.; Kahn, M.; Mitra, A. G. *J. Org. Chem.* 1978, 43, 2923-2925.

Experimental

General

Thin layer chromatograms were run on Silicycle P1120-100 plastic-backed thin layer chromatography plates. The solvent system for development of the thin layer chromatography was: 60% ethyl acetate, 39% hexane, and 1% methanol. The silica gel used for the column chromatography were Silicycle 60 (230-400 mesh) silica gel for the residue from cold and hot ethanol percolation of wood chips, and BDH silica gel for chromatography, 60-120 mesh for the extraction of the mother liquor described in Step 2.

Extraction of Quassin/Neoquassin from Bitterwood Chips

Bitterwood chips that were prepared for the commercial trade (493 g) were percolated in cold ethanol (1.86 L). After 24 hours, the ethanol was evaporated and wood chips were again percolated with cold ethanol. The extraction was over 6 days, after which period, a residue containing quassin/neoquassin (23.94 g, 5% from wood chips) was obtained.

Extraction of a Crystalline Mixture of Quassin/Neoguassin from the Residue

The residue extracted from Bitterwood by cold percolation with ethanol (4.3 g) was suspended in warm water (75 mL) and washed with hexane (2×20 mL). The hexane fraction was evaporated leaving a residue (0.2 g), a thin layer chromatogram of which showed the presence of only non-polar substances, with Rf values higher than that of a quassin/neoquassin mixture.

The aqueous fraction from above was saturated with NaCl and extracted with ethyl acetate (3×50 mL). The ethyl acetate fraction was washed with a little water to remove traces of salt in the fraction (2×15 mL), the washings tasted bitter, indicating that a little of the quassin/neoquassin mixture was being removed in the washings.

Evaporation of the ethyl acetate gave a residue (0.43 g), the thin layer chromatogram of which showed the presence of primarily a quassin/neoquassin mixture. The mixture crystallized from ethanol as prisms (0.052 g, 0.06% from wood chips). The mother liquor was concentrated (0.35 g), and stored for a further separation.

Separation of the Residue from the Mother Liquor after the First Crystallization of Quassin/Neoquassin The residue from the mother liquor, after the first crystallization of quassin/neoquassin (0.264 g) was dissolved in a minimum volume of ethanol (2 mL) and loaded onto a column of silica (4.51 g), a ratio of 17:1, silica to residue.

The first fraction was obtained by eluting with hexane (30 mL), the second by elution with ethyl acetate (50 mL), and the third by ethanol (50 mL). Thin layer chromatography of fraction one, showed only non-polar substances. Fraction two was rich with the quassin/neoquassin mixture, and fraction three, primarily polar substances, with only a trace of quassin/neoquassin.

Seeding of the residue from fraction two, with a few crystals of the quassin/neoquassin mixtures resulted in crystallization (0.044 g, 0.066% from wood chips), of a mixture identical to the crystalline mixture of quassin/neoquassin previously obtained and confirmed by thin layer chromatography.

Percolation of Wood Chips With Hot Ethanol and Column Chromatography of the Extracted Residue Dried wood chips of *Picrasma excelsa* (351 g) were refluxed with ethanol (4×1.5 L) at 78° C., for five hours. Evaporation of the ethanol in vacuo yielded a residue (15 g, 4.27%). A portion of the residue (1.0 g) was placed on a silica gel (58 g) column and eluted with a solvent mixture containing dichloromethane-ethyl acetate-methanol in a ratio of 96:3:1. The fractions that were indicated by thin layer chromatography to contain quassin and neoquassin were combined and subjected to repeated column chromatography starting with the eluting solvent described above and ending with a mixture of dichloromethane-ethyl acetate-methanol, 66:19:15. The fractions containing quassin/neoquassin crystallized from ethyl acetate:hexane, 95:5 (0.005 g, 0.021% of the wood chips). Thin layer chromatography indicated a mixture of quassin/neoquassin.

Percolation of Wood Chips with Cold Ethanol and Column Chromatography of the Extracted Residue Dried wood chips of *Picrasma excelsa* (1000 g) were percolated with cold ethanol (4×4 L) over four days, then evaporated in vacuo to a residue (25 g). A portion of the residue (14.7 g) was suspended in water (ca. 200 mL) and extracted successively with hexane, ethyl acetate, and dichloromethane, each 150 mL. The hexane fraction, which contained only non-polar constituents was set aside and the ethyl acetate and dichloromethane fractions were combined and evaporated to a residue (5.7 g). Column chromatography of the residue in the manner described above from the percolation with refluxing ethanol, gave a concentrated fraction which yielded a crystalline mixture of quassin/neoquassin from ethyl acetate: hexane 95:5 (0.602 g, 0.102%).

Extraction Using an Ultrasonic Bath

These extractions were done using a Branson, model 3210 ultrasonic bath.

Bitterwood chips (319 g.) were placed in the ultrasonic bath with a 1:1 mixture of ethanol:water as extracting solvent (3.0 L) and subjected to ultrasonic agitation for 24 hours. After sonification, most of the ethanol was removed with a rotary evaporator, and the remaining, largely aqueous, solution extracted with hexane. The thin layer chromatography of the residue from the hexane extract (1.21 g, 0.38% w/w based on the wood chips) indicated only fairly non-polar substances and none of the active ingredients of quassin/neoquassin. After extraction with hexane, the aqueous solution was saturated with NaCl, and extracted with ethyl acetate to yield a residue (1.1 g, 0.34% w/w based on wood chips), the thin layer chromatography of which showed the presence of mainly the active ingredients of quassin/neoquassin.

Two similar extractions were performed. The first extraction was over a period of twelve hours and provided an actual yield of 45%, as compared to that after sonification for 24 hours. The second extraction was over a period of 48 hours and provided an actual yield of 91%, as compared to that after sonification for 24 hours. The twelve hour test, in comparison to the 24 hour test above, indicated that sonification after 12 hours resulted in an incomplete extraction. The 48 hour test in comparison with the 24 hour test indicated that the process was essentially complete after 24 hours, and that no additional quassin/neoquassin was obtained after this period. In support of this conclusion, the wood chips after 24 hours of sonification were completely tasteless.

Clarification Using Decolorizing Charcoal

Decolorizing charcoal used was BDH's laboratory reagent grade.

A portion of the residue resulting from sonification of the wood chips for 24 hours (0.25 g) was dissolved in ethanol (5 mL). Decolorizing charcoal (0.012 g, 4.8%) was added to this solution and the resulting suspension stirred overnight with a magnetic stirrer. The mixture was then filtered through Kieselghur and the solvent evaporated from the filtrate to leave a pale yellow residue (0.23 g).

In other experiments decolorizations were performed in ethyl acetate with a 4.8% w/w ratio of decolorizing charcoal/residue, and in another with a 2.5% w/w charcoal/residue ratio, in ethanol. All other conditions were as previously described above. In both cases evaporation of solvent gave approximately the same yield of pale yellow residues to that obtained in the first experiment.

Seeding of the above residues in a solution of ethanol, with mixed crystals of quassin/neoquassin and leaving the mixture to evaporate very slowly to dryness, resulted in a pale yellow crystalline mass, the thin layer chromatography of which indicated primarily a mixture of quassin/neoquassin.

Flash Chromatography of the Decolorized Product

A sample of the decolorized crystalline mixture (0.141 g) obtained as described above was dissolved in 1:1 ethyl acetate-methanol (1 mL) and the solution applied to a column of silica gel (230-400 mesh, 10 g; height column=45 cm, diameter=1 cm) packed with pressure in ethyl acetate-hexane-methanol, 60:39:1. Flash column chromatography methodology was used, and 40 fractions of volume 3 mL were collected. Analysis by thin layer chromatography indicated that fractions 7-25 consisted of quassin/neoquassin. These fractions were combined and evaporated to dryness to afford quassin/neoquassin (0.055 g, 39%).

Having now described embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of processing quassinoid(s) from plant material selected from the group consisting of *Picrasma excelsa, Quassia amara, Picrasma quassioides, Quassia africana* and mixtures thereof comprising:
    adding a first solvent to said plant material;
    mixing said first solvent and said plant material;
    evaporating said first solvent to yield a residue;
    adding water to said residue and washing with a second solvent, to yield an aqueous fraction;
    saturating said aqueous fraction with a polarity increasing agent and extracting with ethyl acetate to yield a second residue;
    subjecting said second residue to crystallization to yield crystalline quassinoid(s) and mother liquor;
    separating said mother liquor with column chromatography; and
    subjecting said separated mother liquor to crystallization to yield additional crystalline quassinoid(s).

2. The method of claim 1, wherein said first solvent is ethanol, and said second solvent is hexane.

3. The method of claim 1, wherein said quassinoid(s) are selected from the group consisting of quassin, neoquassin, and combinations thereof.

4. The method of claim 1, wherein neither said first solvent nor said second solvent is selected from the group of solvents consisting of chloroform, methanol, and diethyl ether.

5. The method of claim 1, wherein said polarity increasing agent is sodium chloride.

6. The method of claim 1, wherein said separating said mother liquor comprises: loading mother liquor on to a chromatography column comprising silica, and using a silica to residue ratio of about 17:1.

7. A method of processing at least one quassinoid from plant material selected from the group consisting of *Picrasma excelsa, Quassia amara, Picrasma quassioides, Quassia africana* and mixtures thereof comprising:
    mixing said plant material in an ultrasonic bath with a water/alcohol mixture;
    evaporating alcohol from said water/alcohol mixture to yield an aqueous phase, and washing said aqueous phase with a first solvent to yield an aqueous fraction;
    saturating said aqueous fraction with a polarity increasing agent and extracting with ethyl acetate to yield a residue;
    adding a second solvent to said residue;
    adding charcoal to yield an at least partially decolorized mixture;
    filtering said at least partially decolorized mixture and evaporating said second solvent to yield a second residue;
    adding a third solvent to said second residue and seeding with crystals of said at least one quassinoid to form a seeded solution;
    allowing said seeded solution to crystallize.

8. The method of claim 7, wherein said first solvent is hexane and wherein said second solvent is ethanol.

9. The method of claim 7, wherein said at least one quassinoid is selected from the group consisting of quassin, neoquassin, and combinations thereof.

10. The method of claim 7, wherein about 2.5% to about 5% of charcoal is added.

11. The method of claim 7, wherein said third solvent is ethanol.

12. The method of claim 7, wherein crystallization occurs through evaporation of said third solvent.

13. The method of claim 7, wherein none of said first solvent, said second solvent, nor said third solvent is selected from the group of solvents consisting of chloroform, methanol, and diethyl ether.

14. The method of claim 7, wherein said polarity increasing agent is sodium chloride.

15. The method of claim 7, wherein said plant material is mixed in said ultrasonic bath with a water/alcohol mixture for about twenty-four hours.

16. A method of processing a quassinoid-containing extract from plant material selected from the group consisting of *Picrasma excelsa, Quassia amara, Picrasma quassioides, Quassia Africana*, and mixtures thereof comprising:
    a) providing an aqueous dispersion of said quassinoid-containing extract;
    b) extracting nonpolar contaminants from said aqueous dispersion with a nonpolar, water-immiscible solvent to yield an aqueous phase containing a quassinoid material;

c) establishing an increased polarity in said aqueous phase from step b) by dissolving therein a quantity of a nontoxic neutral salt;

d) extracting said quassinoid material from said aqueous phase from step c) with a water-immiscible organic solvent for said quassinoid material to yield an organic phase containing said quassinoid material substantially devoid of polar contaminants.

17. The method of claim 16, wherein said quassinoid material comprises at least one quassinoid composition selected from the group consisting of quassin, neoquassin, and mixtures thereof.

18. The method of claim 16, wherein said aqueous dispersion of said quassinoid extract is prepared by extracting said plant material with a solvent for said quassinoid material, subsequently removing said solvent to yield a solid quassinoid extract, and dispersing said solid quassinoid extract in water.

19. The method of claim 16, wherein said aqueous dispersion of said quassinoid extract is prepared by extracting said plant material with a solvent for said quassinoid material, said solvent comprising a mixed solvent including water and a water-miscible organic solvent, to yield a dispersion of said quassinoid composition in said mixed solvent, and subsequently removing said water-miscible organic solvent from said dispersion to yield said aqueous dispersion of said quassinoid extract.

20. The method of claim 19, wherein said water-miscible organic solvent is a volatile organic solvent, and said volatile organic solvent is removed from said mixed solvent by evaporation.

21. The method of claim 20, wherein said volatile organic solvent is ethanol.

22. The method of claim 16, further comprising e) crystallizing said quassinoid compound from said organic phase from step d).

23. The method of claim 22, wherein said crystallizing in step e) is conducted by f) evaporating said organic solvent from said organic phase from step d) to yield a residue containing said quassinoid; g) crystallizing said residue from step f) to yield crystalline quassinoid.

24. The method of claim 23, wherein step g) is conducted by dissolving said residue from step f) in a suitable solvent to yield a quassinoid solution and crystallizing said quassinoid from said quassinoid solution to yield crystalline quassinoid and a mother liquor.

25. The method of claim 24, comprising recovering additional quassinoid from said mother liquor by separating said quassinoid from said mother liquor by column chromatography.

26. The method of claim 25, said recovering additional quassinoid from said mother liquor comprising:

h) evaporating solvent from said mother liquor to yield a residue;

i) dissolving said residue from step h) in a lower aliphatic alcohol solvent to yield a solution of said residue, j) applying a quantity of said solution from step i) to a silica gel chromatographic column in an amount to provide a ratio of said silica gel to said residue contained in said solution of about 15:1 to about 20:1, by weight;

k) eluting nonpolar impurities with a first eluting solvent which is a pure nonpolar organic eluting solvent;

l) subsequently eluting said quassinoid with a second pure organic eluting solvent of greater polarity than said first organic eluting solvent;

m) crystallizing said quassinoid from said second organic eluting solvent.

27. The method of claim 26, wherein said ratio of said silica gel to said residue is about 17.

28. The method of claim 16, further comprising n) removing said water-immiscible organic solvent from said organic phase to yield a residue containing said quassinoid material;

o) dissolving said residue from step n) in a solvent for said quassinoid material selected from the group consisting of lower aliphatic alcohols to yield a solution of said quassinoid material in said solvent;

p) decolorizing said solution of quassinoid material from step o) with decolorizing charcoal to yield a solution of decolorized quassinoid material;

q) removing said decolorizing charcoal from said solution of said decolorized quassinoid material;

r) removing said solvent from said solution of said decolorized quassinoid material to yield a residue comprising said decolorized quassinoid material;

s) crystallizing said residue from step r) to yield a commercially acceptable substantially crystalline quassinoid material.

29. The method of claim 28, wherein said crystallizing step (s) includes t) dissolving said decolorized quassinoid material from step r) in a solvent therefor selected from lower aliphatic alcohols to yield a solution of said quassinoid material in said solvent therefor;

u) seeding said solution of quassinoid material from step t) with crystals of a quassinoid compound;

v) allowing said solvent to evaporate from said seeded solution at room temperature to yield a solid quassinoid composition containing said quassinoid material.

30. A method of processing an extract derived from plant material selected from the group consisting of *Picrasma excelsa, Quassia amara, Picrasma quassioides, Quassia Africana*, and mixtures thereof containing at least one quassinoid comprising:

extracting nonpolar contaminants from a dispersion of said extract in a first solvent, with a second solvent, wherein said second solvent is immiscible in said first solvent and wherein said second solvent has a lower polarity than said first solvent, to yield a first phase containing a quassinoid material;

adding a polarity increasing agent to said first phase to yield a second phase;

extracting said second phase with a water immiscible organic solvent to yield a second residue;

subjecting said second residue to crystallization to yield crystalline quassinoid(s).

31. The method of claim 30, wherein said polarity increasing means is a salt.

* * * * *